United States Patent [19]

Leveque et al.

[11] Patent Number: 5,262,407
[45] Date of Patent: Nov. 16, 1993

[54] USE OF SALICYLIC DERIVATIVES FOR THE TREATMENT OF SKIN AGING

[75] Inventors: Jean L. Leveque, Le Raincy; Didier Saint Leger, Paris, both of France

[73] Assignee: L'Oreal, Paris, France

[21] Appl. No.: 780,063

[22] Filed: Oct. 21, 1991

Related U.S. Application Data

[63] Continuation of Ser. No. 451,372, Dec. 15, 1989, abandoned.

[30] Foreign Application Priority Data

Dec. 16, 1988 [LU] Luxembourg ............... 87408

[51] Int. Cl.$^5$ ............................................. A61K 31/60
[52] U.S. Cl. ................................................. 514/159
[58] Field of Search ..................................... 514/159

[56] References Cited

U.S. PATENT DOCUMENTS 4,603,146 7/1986 Kligman ................. 514/159

FOREIGN PATENT DOCUMENTS 0124905 11/1984 European Pat. Off. .

*Primary Examiner*—Leonard Schenkman
*Attorney, Agent, or Firm*—Cushman, Darby & Cushman

[57] ABSTRACT

The invention relates to a composition intended for the treatment of skin aging, containing, in a physiologically acceptable medium, at least one salicylic acid derivative corresponding to the formula:

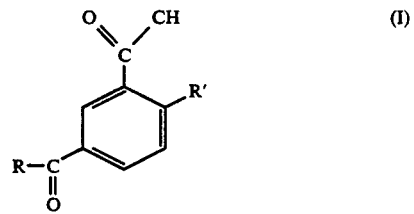

in which:

R represents a saturated aliphatic chain or an unsaturated chain bearing one or more conjugated or unconjugated double bonds, it being possible for the chains to be substituted with one or more halogen atoms as well as with trifluoromethyl groups, with one or more hydroxyl groups in free form or a form esterified by an acid, or alternatively with a carboxyl group, free or esterified by a lower alcohol; and R' represents a hydroxyl group or an ester group of formula:

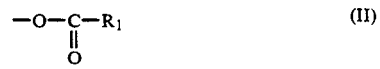

where $R_1$ is a saturated or unsaturated aliphatic group.

11 Claims, No Drawings

USE OF SALICYLIC DERIVATIVES FOR THE TREATMENT OF SKIN AGING

This is a continuation of application Ser. No. 07/451,372, filed Dec. 15, 1989, abandoned.

The present invention relates to new compositions intended for treating skin aging, employing salicylic acid derivatives.

During the aging process, the appearance on the skin of different signs very characteristic of aging, reflected, in particular, in a modification of skin structure and function, is observed. These signs are especially pronounced on uncovered areas such as face and hands, on which special characteristics due to exposure of the skin to sunlight (actinic aging) are generally added.

On an uncovered area, it is difficult, in general, to distinguish clearly between signs originating from the physiological process of skin aging and signs due to repeated exposure of the skin to light.

The main clinical signs of skin aging are the following: appearance of deep wrinkles, increasing with age. A disorganization of the "grain" of the skin is noted, that is to say the micro-relief is less regular and is anisotropic in nature.

The skin color is generally modified, appearing paler and yellower, which appears to be due chiefly to a disorganization of the microcirculation (less haemoglobin in the papillary layer of the dermis). Numerous colored spots appear at the surface, which is due to impaired melanogensis. On some areas, diffuse irritation and sometimes telangiectasia are present.

Another clinical sign of aging is the dry and rough appearance of the skin, which is due chiefly to greater desquamation, these squamae contributing also to the somewhat grey appearance of the color by diffracting light rays.

Finally, a loss is noted in firmness and tonus of the skin, which, as in the case of wrinkles, is explained at least partially by a dermal and epidermal atrophy as well as a flattening of the dermoepidermal formation.

It is hence noted that the clinical signs of skin aging result chiefly from a dysfunction of the main biological mechanisms operating in the skin.

The applicant discovered, surprisingly, that the use of salicylic acid derivatives enabled this aging to be retarded and the clinical signs of the latter to be effected.

They found, more especially, that, by means of these salicylic derivatives, it was possible to lessen wrinkling at least, to modify the color of the skin, which appears more pinkish, to obliterate surface pigmented spots, to eliminate squamae and to give a more elastic consistency to the skin. It was found, in particular, that it was possible to impart a much softer feel to the skin.

The salicylic acid derivatives which are usable according to the invention are known per se, and have already been described in the prior art as capable of being used in topical compositions in the field of cosmetology and dermopharmacy, and more especially as therapeutic and comedolytic agents such as those for the treatment of acne.

The applicants have now discovered a new therapeutic application acting on a biological mechanism completely different from that of acne, which is mainly encountered in young individuals.

The subject of the invention is hence mainly the use of salicylic acid derivatives for the treatment of skin aging.

Another subject of the invention consists of the compositions employed.

Other subjects of the invention will become apparent on reading the description and examples which follow.

The salicylic acid derivatives which are usable according to the invention for the treatment of skin aging correspond essentially to the following general formula:

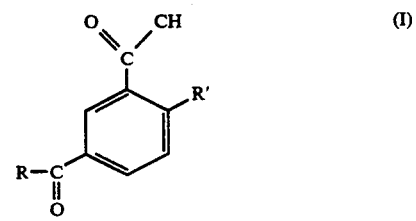

in which:

R represents a linear, branched or cyclized saturated aliphatic chain having from 3 to 11 carbon atoms, or an unsaturated chain having from 3 to 17 carbon atoms, bearing one or more conjugated or unconjugated double bonds, it also being possible for the above chains to be substituted with one or more halogen atoms as well as with trifluoromethyl groups, with one or more hydroxyl groups in free form or a form esterified by an acid having from 1 to 6 carbon atoms, or alternatively with a carboxyl group, free or esterified by a lower alcohol having from 1 to 6 carbon atoms, it being possible for these different groups to be present simultaneously on the said substituents; and R' represents a hydroxyl group or an ester group corresponding to the formula:

in which $R_1$ is a saturated or unsaturated aliphatic group having from 1 to 18 carbon atoms.

More especially preferred compounds are those corresponding to the formula (I) above in which R' denotes a hydroxyl group and R an alkyl group having from 3 to 11 carbon atoms.

Other especially advantageous compounds are those in which R represents a chain derived from linoleic, linolenic or oleic acid.

Another group of especially preferred compounds consists of the compounds in which R denotes an alkyl chain having from 3 to 11 carbon atoms and bearing a free, esterified or salified carboxyl group and R' denotes a hydroxyl group.

Especially advantageous compounds according to the invention are selected from 5-n-octanoylsalicylic acid, 5-n-dodecanoylsalicylic acid and 5-n-decanoylsalicylic acid, it being possible for these compounds to be optionally used in micronized form.

Trials performed by the applicants have enabled it, in particular, to be shown that the compounds according to the invention have an especially exceptional angiogenic effect.

It is found that application of the composition based on 5-n-octanoylsalicylic acid produces a large increase in capillary volume and number.

The compositions, used according to the invention in the treatment of skin aging, contain at least one salicylic acid derivative of the formula (I) defined above in a physiologically acceptable medium, and are generally presented in the form of gels, creams, lotions, sticks, foams or soaps, or may be pressurized in aerosol devices.

They can contain water and/or solvents compatible with the skin, for example $C_1$–$C_4$ lower alcohols such as ethanol and isopropanol, or polyhydric alcohols such as propylene glycol and glycerol, these solvents being present in proportions of between 5 and 99% by weight.

They may also be presented in the form of fatty compositions containing oils or fats such as vaseline and triglycerides.

The compound of formula (I) according to the invention is preferably present in these compositions in proportions of between 0.1 and 10% by weight.

These compositions can also contain thickeners, demulcents, superfatting agents, emollients, wetting agents, surfactants, preservatives, antifoams, sunscreens, oils, waxes, colorings and/or pigments whose function is to color the skin or the composition itself, antioxidants and any other ingredient customarily used in compositions intended for topical application.

Especially preferred compositions are anhydrous gels, creams and fatty ointments or milks comprising, in addition to the compounds defined above, fatty alcohols, oxyethylenated or polyglycerolated fatty alcohols, fatty acid esters, natural or synthetic oils, waxes.

In the treatment of skin aging, these compositions are more especially applied to areas exposed to light, on the basis of 1 to 10 mg $cm^2$ of skin and for a period which can range from one week to 20 weeks or longer.

The compositions according to the invention can also contain other active substances having an effect on skin aging, such as, more especially, retinoids such as, for example, all-trans-retinoic acid, 13-cis-retinoic acid, retinol, retinal and their derivatives. It is also possible to apply these derivatives in two stages, successively or separated by a period of time.

The examples which follow are designed to illustrate the invention without, however, being restrictive in nature.

EXAMPLE 1

The following composition is prepared:

| | |
|---|---|
| Propylene glycol | 45.00 g |
| 5-n-Octanoylsalicylic acid | 3.00 g |
| KLUCEL H (hydroxypropylcellulose) sold by the company HERCULES | 1.50 g |
| Anhydrous ethanol | qs 100.00 g |

This composition is presented in the form of a gel.

EXAMPLE 2

The following composition is prepared:

| | |
|---|---|
| Propylene glycol methyl ether | 37.00 g |
| Hydroxypropylcellulose | 1.50 g |
| 5-n-Octanoylsalicylic acid | 3.00 g |
| Anhydrous ethanol | qs 100.00 g |

This composition is presented in the form of a gel.

EXAMPLE 3

The following composition is prepared:

| | |
|---|---|
| Propylene glycol methyl ether | 35.00 g |
| Hydroxyethylcellulose | 1.50 g |
| 5-n-Octanoylsalicylic acid | 5.00 g |
| Anhydrous ethanol | qs 100.00 g |

This composition is presented in the form of a gel.

EXAMPLE 4

The following composition is prepared:

| | |
|---|---|
| Propylene glycol | 35.00 g |
| Hydroxypropylcellulose | 1.50 g |
| 5-n-Octanoylsalicylic acid | 5.00 g |
| Anhydrous ethanol | qs 100.00 g |

This composition is presented in the form of a gel.

EXAMPLE 5

The following composition is prepared:

| | |
|---|---|
| Vaseline | 65.00 g |
| 5-n-Octanoylsalicylic acid | 5.00 g |
| Perhydrosqualene | qs 100.00 g |

This composition is usable in the form of a fatty ointment.

EXAMPLE 6

The following composition is prepared:

| | |
|---|---|
| Propylene glycol | 5.00 g |
| 5-n-Octanoylsalicylic acid | 4.00 g |
| Acrylic acid crosslinked with a polyfunctional agent, sold by the company GOODRICH under the name CARBOPOL 940 | 0.80 g |
| NaOH | 0.125 g |
| Water | qs 100.00 g |

The 5-n-octanoylsalicylic acid is used in micronized form with a particle size of less than 5 1.

This composition is presented in the form of a gel.

EXAMPLE 7

The following composition is prepared:

| | |
|---|---|
| Glycerol monostearate | 0.80 g |
| Cetyl alcohol | 2.00 g |
| Cetyl/stearyl alcohol | 5.00 g |
| Polyoxyethylene stearate, sold by the company ATLAS under the trade name MYRJ 49 | 3.00 g |
| Acrylic acid crosslinked with a polyfunctional agent, sold by the company GOODRICH under the name CARBOPOL 941 | 0.50 g |
| Triethanolamine | 0.30 g |
| MIGLYOL 810, sold by the company DYNAMIT NOBEL | 12.00 g |
| Preservative | qs |
| 5-n-Octanoylsalicylic acid | 6.00 g |
| Water | qs 100.00 g |

This composition is used as a moisturizing cream.

EXAMPLE 8

The following composition is prepared:

| | |
|---|---|
| 5-n-Octanoylsalicylic acid | 4.00 g |

| | |
|---|---|
| Polyethylene glycol 400 | 18.50 g |
| Propylene glycol methyl ether | 18.50 g |
| Hydroxypropylcellulose | 1.50 g |
| Anhydrous ethanol | qs 100.00 g |

This composition is presented in the form of a gel.

EXAMPLE 9

The following composition is prepared:

| | |
|---|---|
| 5-n-Octanoylsalicylic acid in micronized form, having a particle size of less than 5 μ | 3.00 g |
| Propylene glycol | 6.00 g |
| Acrylic acid crosslinked with a polyfunctional agent, sold by the company GOODRICH under the name CARBOPOL 940 | 0.80 g |
| NaOH | 0.125 g |
| Water | qs 100.00 g |

This composition is presented in the form of a gel.

It is found that, when these compositions are applied to skin displaying clinical signs of aging, the appearance of the skin assumes a more pinkish color, the wrinkling is lessened and spots such as senile lentigo disappear.

It may be concluded from these results that these compositions have an anti-aging effect.

These compositions also permitted the observations to be made, by measurement of the skin fold on OLAC male mice, of a distinct increase in the thickness of this fold following a treatment consisting in applying these compositions on the basis of 5 days per week for two and ½ months.

We claim:

1. A method for the treatment of the skin to lessen wrinkling, modify its color, reduce surface pigmented spots, eliminate squamae, or impart a softer feel to the skin comprising applying to the skin in an amount effective to treat said skin a composition comprising, in a physiologically acceptable medium, at least one salicylic acid derivative having the formula

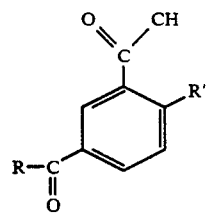

(I)

wherein

R represents a linear, branched or cyclized saturated aliphatic chain having from 3 to 11 carbon atoms, and R' represents a hydroxyl group or an ester group having the formula

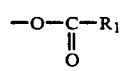

(II), wherein $R_1$ is a saturated or unsaturated aliphatic group having from 1 to 18 carbon atoms, said salicylic acid derivative being present in an amount ranging from 0.1 to 10 percent by weight relative to the total weight of said composition.

2. The method of claim 1 where, in the salicylic acid derivative of formula I, R' represents a hydroxyl group and R represents alkyl having from 3 to 11 carbon atoms.

3. The method of claim 1 wherein said salicylic acid derivative of formula I is selected from the group consisting of 5-n-octanoylsalicylic acid, 5-n-dodecanoylsalicylic acid and 5-n-decanoylsalicylic acid.

4. The method of claim 1 wherein the composition is in the form of a gel, cream, milk, stick, foam, soap, oil, fatty composition, lotion or pressurized in an aerosol device.

5. The method of claim 1 wherein the composition also includes at least one of a thickener, a demulcent, a superfatting agent, an emollient, a wetting agent, a surfactant, a preservative, an antifoam agent, a sunscreen, an oil, a wax, a coloring agent for coloring the said composition or skin, a pigment for coloring said composition or skin or an antioxidant.

6. The method of claim 1 wherein the composition also includes a retinoid.

7. The method of claim 1 wherein the composition is in the form of an anhydrous gel containing a thickening agent, a lower alcohol and a polyhydric alcohol.

8. The method of claim 1 wherein the composition is in the form of a fatty ointment.

9. The method of claim 1 wherein the composition is in the form of a cream.

10. The method of claim 1 wherein said composition is applied to the skin in an amount ranging from 1 to 10 mg/cm² of skin for a period of time ranging from one week to about 20 weeks.

11. A method of treatment of actinic aging of the skin due to repeated exposure of the skin to sunlight comprising applying to the skin in an amount effective to treat the skin a composition comprising, in a physiologically acceptable medium, at least one salicylic acid derivative having the formula

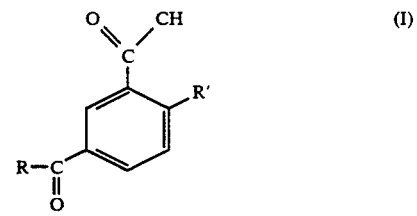

(I)

wherein

R represents a linear, branched or cyclized saturated aliphatic chain having from 3 to 11 carbon atoms, and R' represents a hydroxyl group or an ester group having the formula:

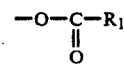

(II), wherein $R_1$ is a saturated or unsaturated aliphatic group having from 1 to 18 carbon atoms, said salicylic acid derivative being present in an amount ranging from 0.1 to 10 percent by weight relative to the total weight of said composition.

* * * * *